(12) United States Patent
Nakamori et al.

(10) Patent No.: US 6,465,228 B1
(45) Date of Patent: Oct. 15, 2002

(54) LEVODIONE REDUCTASE

(75) Inventors: Shigeru Nakamori, Fukui-ken; Sakayu Shimizu, Kyoto; Masaru Wada, Fukui-ken, all of (JP)

(73) Assignee: Roche Vitamins, Inc., Parsippany, NJ (US)

( * ) Notice: Subject to any disclaimer, the term of this patent is extended or adjusted under 35 U.S.C. 154(b) by 0 days.

(21) Appl. No.: 09/495,523

(22) Filed: Jan. 31, 2000

(30) Foreign Application Priority Data

Feb. 1, 1999 (EP) .............................. 99102037

(51) Int. Cl.⁷ ................................ C12N 9/02
(52) U.S. Cl. ...................... 435/189; 435/170; 435/171
(58) Field of Search ............................... 435/189, 170, 435/171

(56) References Cited

U.S. PATENT DOCUMENTS 4,026,949 A * 5/1977 Boguth ...................... 435/123

FOREIGN PATENT DOCUMENTS

EP    0 982 406 A2    3/2000

OTHER PUBLICATIONS

Demain et al. Manufal of Industrial Microbiology and Biotechnology, 1986, ASM, pp. 406–407 and 444–445.*
Wada et al., "Purification and Characterization of Monovalent Cation–Activated Levodione Reductase from *Corynebacterium aquaticum* M–13," *Applied and Environment Microbiology*, vol. 65, No. 10, pp. 4399–4403 (1999).
Nishii, et al., "Microbial conversion of dihydrooxoisophorone (DOIP) to 4–hydroxy–2,2,6–trimethylcyclohexanone (4–HTMCH) by thermophilic bacteria," *J. Biotechnology*, vol. 9, pp. 117–128 (1989).

* cited by examiner

*Primary Examiner*—Irene Marx
(74) *Attorney, Agent, or Firm*—Bryan Cave LLP

(57) ABSTRACT

A levodione reductase having the following physical properties is provided: molecular weight: from about 142,000 to about 155,000±10,000 (consisting of four homologous subunits having a molecular weight of 36,000±5,000); co-factor: nicotinamide adenine dinucleotide (AND/NADH); substrate specificity: active on levodione; optimum temperature: about 15° C. to about 20° C. at pH 7.0; optimum pH: 7.5; and activator: $K^+$, $Cs^+$, $Rb^+$, $Na^+$ and $NH_4^+$. The levodione reductase according to the present invention produces actinol, an important intermediate for the production of zeaxanthin, from levodione. This enzyme may be produced from a microorganism belonging to the genus Corynebacterium, preferably the microorganism *Corynebacterium aquaticum* AKU 611 (FERM BP-6448) or a functional equivalent, subculture, mutant or variant thereof. Also provided is a process for producing the levodione reductase that includes cultivating a microorganism of the genus Corynebacterium in an aqueous medium under aerobic conditions, disrupting the cells of the microorganism and isolating and purifying the levodione reductase from the cell-free extract. A process for producing actinol from levodione is also provided that includes contacting levodione with levodione reductase in the presence of the reduced form of nicotinamide adenine dinucleotide or a cell-free extract of the microorganism, and then isolating the resulting actinol from the reaction mixture.

8 Claims, No Drawings

LEVODIONE REDUCTASE

FIELD OF THE INVENTION

The present invention relates to a novel enzyme, in particular a levodione reductase (hereinafter referred to as LR), a process for producing the enzyme, and a process for producing (4R, 6R)-4-hydroxy-2,2,6-trimethylcyclohexanone (hereinafter referred to as actinol) from (6R)-2,2,6-trimethylcyclohexane-1,4-dione (hereinafter referred to as levodione) utilizing the enzyme.

BACKGROUND OF THE INVENTION

Actinol is an important intermediate for the production of zeaxanthin. European Patent Application Nos. 98115564.1 and 99115723.1 disclose processes for the manufacture of actinol. Such processes include contacting levodione with a microorganism selected from Cellulomonas, Corynebacterium, Planococcus and Arthrobacter which is capable of the selective asymmetric reduction of levodione to actinol. The resulting actinol from the reaction mixture is recovered therefrom. *Corynebacterium aquaticum* AKU611 (FERM BP-6448) was found to be one of the best microorganism strains for this purpose.

*Corynebacterium aquaticum* AKU611 has the following taxonomical properties:

| | |
|---|---|
| 1) Growable temperature | 15–40° C. |
| 2) Optimum temperature for growth | 30° C. |
| 3) Obligatory aerobic and gram negative microorganism | |
| 4) Spore formation | None |
| 5) Polymorphism and traditional rod-cocus cycles may be observed during cultivation | |
| 6) Motility | None |

Moreover, the strain *Corynebacterium aquaticum* AKU611 was identified as having these characteristics based on assimilation of various carbon sources by the Biolog System (Biolog Inc., Hayward, Calif., see also Nature Vol. 339, 157–158, May 11, 1989) as follows: 96-well microtiterplates were inoculated with *Corynebacterium aquaticum* cells and incubated for 24 hours at 28° C. Each well contained one of the 96 types of carbon sources in BUGM+B medium (Biolog Universal Growth Media+Blood) (Biolog Inc.).

After incubation, the strain showed the following assimilation of carbon sources:

| C Source | Assimilation | C Source | Assimilation |
|---|---|---|---|
| A1 | − | A2 | − |
| A3 | − | A4 | − |
| A5 | − | A6 | − |
| A7 | − | A8 | + |
| A9 | + | A10 | − |
| A11 | − | A12 | + |
| B1 | − | B2 | + |
| B3 | − | B4 | − |
| B5 | + | B6 | − |
| B7 | + | B8 | − |
| B9 | + | B10 | + |
| B11 | + | B12 | − |
| C1 | − | C2 | + |
| C3 | − | C4 | + |
| C5 | + | C6 | + |
| C7 | − | C8 | + |
| C9 | − | C10 | − |
| C11 | − | C12 | − |
| D1 | − | D2 | − |
| D3 | + | D4 | − |
| D5 | + | D6 | − |
| D7 | − | D8 | + |
| D9 | − | D10 | − |
| D11 | + | D12 | + |
| E1 | − | E2 | − |
| E3 | + | E4 | − |
| E5 | − | E6 | − |
| E7 | − | E8 | − |
| E9 | − | E10 | − |
| E11 | − | E12 | − |
| F1 | − | F2 | − |
| F3 | − | F4 | − |
| F5 | − | F6 | + |
| F7 | − | F8 | − |
| F9 | − | F10 | − |
| F11 | − | F12 | − |
| G1 | − | G2 | − |
| G3 | − | G4 | − |
| G5 | − | G6 | − |
| G7 | − | G8 | − |
| G9 | − | G10 | − |
| G11 | − | G12 | − |
| H1 | − | H2 | − |
| H3 | − | H4 | − |
| H5 | − | H6 | − |
| H7 | − | H8 | − |
| H9 | − | H10 | − |
| H11 | − | H12 | − |

In the table, "+" indicates that the carbon source was assimilable and "−" indicates that it was not assimilable.

The alpha-numeric codes set forth above are defined in the table below:

| | | | |
|---|---|---|---|
| A1 | Water | A2 | α-cyclodextrin |
| A3 | β-cyclodextrin | A4 | Dextrin |
| A5 | Glycogen | A6 | Inulin |
| A7 | Mannan | A8 | TWEEN ® 40 |
| A9 | TWEEN ® 80 | A10 | N-acetyl-D-glucosamine |
| A11 | N-acetyl-D-mannosamine | A12 | Amygdalin |
| B1 | L-arabinose | B2 | D-arabitol |
| B3 | Arbutin | B4 | Cellobiose |
| B5 | D-fructose | B6 | L-fucose |
| B7 | D-galactose | B8 | D-galacturonic acid |
| B9 | Gentiobiose | B10 | D-gluconic acid |
| B11 | α-D-glucose | B12 | m-inositol |
| C1 | α-D-lactose | C2 | Lactulose |
| C3 | Maltose | C4 | Maltotriitrose |
| C5 | D-mannitol | C6 | D-mannose |
| C7 | D-melezitose | C8 | D-melibiose |
| C9 | α-methyl-D-galactoside | C10 | α-methyl-D-galactoside |
| C11 | 3-methyl-glucose | C12 | α-methyl-D-glucoside |
| D1 | β-methyl-D-glucoside | D2 | α-methyl-D-mannoside |
| D3 | Palatinose | D4 | D-psicose |
| D5 | D-raffinose | D6 | L-rhamnose |
| D7 | D-ribose | D8 | Salicin |
| D9 | Sedoheputulosan | D10 | D-sorbitol |
| D11 | Stachyose | D12 | Sucrose |
| E1 | D-tagatose | E2 | D-trehalose |
| E3 | Turanose | E4 | Xylitol |
| E5 | D-xylose | E6 | acetic acid |
| E7 | α-hydroxybutyric acid | E8 | β-hydroxybutyric acid |
| E9 | γ-hydroxybutyric acid | E10 | p-hydroxy-phenylacetic acid |
| E11 | α-keto-glutaric acid | E12 | α-keto-valeric acid |
| F1 | Lactamide | F2 | D-lactic acid methyl ester |
| F3 | L-lactic acid | F4 | D-malic acid |

| | | | |
|---|---|---|---|
| F5 | L-malic acid | F6 | methyl pyruvate |
| F7 | Monomethyl succinate | F8 | propionic acid |
| F9 | Pyruvic acid | F10 | Succinamic acid |
| F11 | Succinic acid | F12 | N-acetyl-L-glutamic acid |
| G1 | Alaninamide | G2 | D-alanine |
| G3 | L-alanine | G4 | L-alanyl-glycine |
| G5 | L-asparagine | G6 | L-glutamic acid |
| G7 | glycyl-L-glutamic acid | G8 | L-pyloglutamic acid |
| G9 | L-serine | G10 | Putrscine |
| G11 | 2,3-butanediol | G12 | Glycerol |
| H1 | Adenosine | H2 | 2'-deoxy-adenosine |
| H3 | Inosine | H4 | Thymidine |
| H5 | Uridine | H6 | Adenosine-5'-monophosphate |
| H7 | thymidine-5'-monophosphate | H8 | Uridine-5'-monophosphate |
| H9 | Fructose-6-phosphate | H10 | Glucose-1-phosphate |
| H11 | Glucose-6-phosphate | H12 | DL-α-glycerol phosphate |

SUMMARY OF THE INVENTION

One embodiment of the present invention provides an isolated and purified enzyme having levodione reductase activity wherein the enzyme includes the following physico-chemical properties:

(a) a molecular weight of about 142,000 to about 155,000±10,000;

(b) a nicotinamide adenine dinucleotide (AND/NADH) co-factor;

(c) a substrate specificity for levodione;

(d) an optimum temperature of about 15° C. to about 20° C. at a pH of about 7.0;

(e) an optimum pH of about 7.5; and (f) wherein the enzyme is activated by $K^+$, $Cs^+$, $Rb^+$, $Na^+$ and $NH_4^+$.

A process for producing an enzyme having levodione reductase activity is also provided wherein the enzyme has the following physico-chemical properties: a molecular weight of about 142,000 to about 155,000±10,000, a nicotinamide adenine dinucleotide (AND/NADH) co-factor, a substrate specificity for levodione, an optimum temperature of about 15° C. to about 20° C. at a pH of about 7.0, an optimum pH of about 7.5, and wherein the enzyme is activated by $K^+$, $Cs^+$, $Rb^+$, $Na^+$ and $NH_4^+$. This process includes cultivating cells of a Corynebacterium in an aqueous nutrient medium under aerobic conditions; and disrupting the cells to form a cell free extract containing the enzyme.

A process is also provided for producing actinol from levodione. This process includes forming a reaction mixture containing levodione and (i) a cell-free extract derived from Corynebacterium containing a levodione reductase or (ii) a levodione reductase having the following physico-chemical properties: a molecular weight of about 142,000 to about 155,000±10,000, a nicotinamide adenine dinucleotide (AND/NADH) co-factor, a substrate specificity for levodione, an optimum temperature of about 15° C. to about 20° C. at a pH of about 7.0, an optimum pH of about 7.5, and which enzyme is activated by $K^+$, $Cs^+$, $Rb^+$, $Na^+$ and $NH_4^+$; adding a reduced form of nicotinamide adenine dinucleotide to the reaction mixture; and isolating actinol from the reaction mixture.

An embodiment provides an isolated and purified levodione reductase derived from *Corynebacterium aquaticum* AKU611 (FERM BP-6448) cells having the following properties:

(a) a molecular weight of about 142,000 to about 155,000±10,000, (b) a AND/NADH cofactor;

(c) a substrate specificity for levodione;

(d) an optimum temperature of about 15° C. to about 20° C. at a pH of about 7.0;

(e) a optimum pH of about 7.5; and (f) the levodione reductase being activated by $K^+$, $Cs^+$, $Rb^+$, $Na^+$ and $NH_4^+$.

DETAILED DESCRIPTION OF THE INVENTION

A purified LR sample prepared according to the Examples presented below has the following physico-chemical properties:

1) Enzyme Activity

The novel LR of the present invention catalyzes the reduction of levodione to actinol in the presence of a co-factor according to the following formula:

It has been determined that the reduced form of nicotinamide adenine dinucleotide phosphate (NADPH) does not work as an electron donor in this reaction system.

A standard enzyme assay for detecting levodione reductase enzyme activity has been used in the present invention. This assay is exemplary of a number of recognized assays for detecting LR activity. The LR activity assay used herein is set forth below:

A basal reaction mixture having a total volume of 500 μl includes 100 μl of 1 M potassium phosphate buffer (pH 7.0), 20 μl of 8 mM NADH in 0.2 mM KOH, 10–40 μl of the enzyme solution (i.e., levodione reductase), and water up to a total of 500 μl. This reaction mixture was incubated for 1 minute at 37° C. Then, 2 μl of 0.5 M levodione solution were added to give a final concentration of 2 mM, and the whole mixture was incubated for 1 minute at 37° C. The levodione reductase enzyme activity was monitored with the decrease of the absorbance of NADH at 340 nm.

In the present invention, one unit of the levodione reductase enzyme activity is defined as the amount of the levodione reductase which catalyzes the oxidation of 1 μmole of NADH per minute.

The AND, NADH, and NADPH used in the example set forth herein were obtained from Oriental Yeast (Tokyo, Japan). The protein concentration was determined using a Bio-Rad protein assay kit (Bio-Rad Laboratories (Hercules, Calif.)

2) Molecular Weight

The molecular weight (MW) of the enzyme was measured with a gel filtration HPLC column Cosmosil 5Diol-300 (nacalai tesque: Kyoto-fu, Japan). The apparent molecular weight of the (whole) enzyme was calculated to be about 142,000 to about 155,000±10,000 in comparison to the molecular weight marker proteins: LMW+HMW gel filtration calibration kit, Amersham Pharmacia Biotech (SE-75184 Uppsala, Sweden); ferritin (MW 440,000), aldolase (MW 158,000), bovine serum albumin (MW 67,000), ovalbumin (MW 43,000), and ribonuclease A (MW 13,700).

When a purified sample of the enzyme was subjected to SDS-polyacrylamide gel electrophoresis (SDS-PAGE), a single band with a molecular weight of about 36,000±5,000 was observed in comparison to the molecular weight marker proteins: LMW Electrophoresis calibration kit, Amersham Pharmacia Biotech; bovine serum albumin (MW 67,000), ovalbumin (MW 43,000), carbonic anhydrase (MW 30,000), soybean trypsin inhibitor (MW 20,100), and α-lactalbumin (MW 14,400). These results indicate that the enzyme (i.e., levodione reductase) is composed of four homologous subunits. The values of the molecular weight of the whole enzyme (142,000–155,000±10,000) and of each subunit (36,000±5,000) were determined by the gel filtration column method and the SDS-PAGE method, allowed.

3) Co-factor

In the present invention, it was established that NADH could serve as a co-factor for this reductive reaction, but that NADPH could not.

4) Substrate Specificity

The substrate specificity of the enzyme was determined using the same enzyme assay method as described under 1, except that various solutions containing different substrates (2 mM final concentration in the reaction mixture) were used instead of levodione. It was shown that levodione was the only substrate for which the enzyme exhibited activity.

TABLE 1

| Substrate | Enzyme Activity (unit/ml) |
| --- | --- |
| Levodione | 5.66 |
| Cyclohexanone | Not detected (ND) |
| 1,2-Cyclohexane-dione | ND |
| 1,3-Cyclohexane-dione | ND |
| 1,4-cyclohexane-dione | ND |
| Cyclopentanone | ND |
| 2-Cyclohexene | ND |
| 1,5,5-Trimethylcyclohexene | ND |
| 1,3-Cyclopentane-dione | ND |
| DL-Mevalonolactone | ND |
| D-Camphor | ND |
| L-Camphor | ND |
| Maleic anhydride | ND |
| 4-Chloro-3-oxo-butanoic acid ethyl ester | ND |

5) Optimum Temperature

The enzyme activities were measured at temperatures from about 2 to about 45° C. The optimum temperature of the enzyme activity was determined to be about 15° C. to about 20° C.

TABLE 2

| Temperature (° C.) | Relative Activity (%) |
| --- | --- |
| 2 | 77.8 |
| 5 | 83.8 |
| 10 | 89.1 |
| 15 | 100.0 |
| 20 | 92.4 |
| 25 | 90.9 |
| 30 | 78.0 |
| 35 | 70.7 |
| 40 | 59.4 |
| 45 | 31.6 |

6) Optimum pH

The correlation between the enzyme activity and the pH values of the reaction mixture was determined using the same enzyme assay method as described in Table 1, except that various pHs and buffers were used and 40 μl of 2.5M KCl solution were added to the reaction mixture. The optimum pH of the enzyme reaction was found to be 7.5 as set forth in Table 3 below.

TABLE 3

| Buffer | PH | Relative Activity (%) |
| --- | --- | --- |
| Potassium phosphate buffer | 5.5 | 59.3 |
| | 6.0 | 68.5 |
| | 7.0 | 78.4 |
| | 7.5 | 100 |
| [4-(2-Hydroxyethyl)-piperazino]-ethanesulphonic acid (HEPES) | 7.0 | 7.2 |
| | 7.5 | 10.0 |
| | 8.0 | 21.7 |
| | 8.5 | 21.9 |
| Tris-Hcl | 8.5 | 6.5 |
| | 9.0 | 3.9 |
| | 10.0 | 1.3 |

7) Effect of Metal Ions

The effect of metal ions on the enzyme activity was investigated using the same enzyme assay method as described for Table 1, except that 100 μl of 1 M Tris-HCl buffer (pH 7.5) were used instead of 100 μl of 1 M potassium phosphate buffer (pH 7.0), and various metal solutions were added to the reaction mixture to give a final concentration of metal between 100 mM and 3 M. As a result, it was established that the enzyme activity was increased about 250-fold in the presence of 3 M RbCl and 1.8 M CsCl as shown in Table 4-1

TABLE 4-1

| Metal | Concentration (mM) | Relative Activity (%) |
| --- | --- | --- |
| NaCl | 3 | 0.4 |
| RbCl (+ 3 mM NaCl) | 100 | 6.4 |
| | 200 | 7.5 |
| | 400 | 23.3 |
| | 800 | 32.6 |
| | 1600 | 66.4 |
| | 1800 | 65.1 |
| | 2000 | 93.2 |
| | 2500 | 93.3 |
| | 3000 | 100 |
| CsCl (+ 3 mM NaCl) | 100 | 5.9 |
| | 200 | 14.3 |
| | 400 | 28.3 |
| | 800 | 48.1 |
| | 1600 | 71.4 |
| | 1800 | 100 |
| | 2000 | 86.8 |
| | 2500 | 88.4 |
| | 3000 | 88.0 |

TABLE 4-2

| Metal | Concentration (mM) | Relative Activity (%) |
| --- | --- | --- |
| None | 0 | 2.8 |
| KCl | 200 | 11.5 |
| | 400 | 22.2 |
| | 800 | 40.5 |
| | 1600 | 45.3 |
| | 1800 | 33.5 |
| | 2000 | 28.4 |
| | 2500 | 25.9 |
| | 3000 | 25.2 |
| NH$_4$Cl | 100 | 6.4 |
| | 200 | 21.3 |
| | 400 | 39.3 |
| | 800 | 67.1 |
| | 1600 | 100 |
| | 1800 | 75.3 |
| NaCl | 100 | 4.2 |
| | 200 | 7.7 |
| | 400 | 19.7 |

TABLE 4-2-continued

| Metal | Concentration (mM) | Relative Activity (%) |
|---|---|---|
| | 800 | 35.9 |
| | 1600 | 75.3 |
| | 1800 | 62.8 |
| | 2000 | 62.8 |
| | 2500 | 53.9 |
| | 3000 | 34.1 |

8) Temperature Stability the enzyme solution was treated at various temperatures for 10 minutes, and the remaining enzyme activities were measured using the same enzyme assay method as described for Table 1. Table 5, it was established that the enzyme was stable up to about 35° C., and deactivated with increasing temperature, becoming completely de-activated at about 55° C.

TABLE 5

| Temperature (° C.) | Relative Activity (%) |
|---|---|
| 0 | 100 |
| 30 | 93.3 |
| 35 | 85.1 |
| 40 | 47.8 |
| 45 | 28.9 |
| 50 | 3.2 |
| 55 | 0 |

9) pH Stability

The enzyme was treated with 1 M buffers of various pHs for 10 minutes at 30° C., and its remaining activity was measured using the same enzyme assay method as described in Section 1 above. The enzyme was found to be most stable in the pH range between about 8.0 and about 8.5 as shown in Table 6.

TABLE 6

| Buffer | PH | Relative Activity (%) |
|---|---|---|
| Bis-tris | 6 | 40.6 |
| | 7 | 71.9 |
| HEPES | 7 | 63.4 |
| | 7.5 | 61.6 |
| | 8 | 91.6 |
| Tris-HCl | 8.5 | 100 |
| | 9 | 85.3 |

10) Michaelis Constant (Km) and Maximum Velocity (Vmax) Values

The Km and Vmax values of the enzyme were measured using levodione and actinol as the substrates. The basic enzyme assay method is the same as described under 1, but the substrate and the enzyme concentrations were varied. The Km and Vmax values against levodione as the substrate were 8.5 mM and 101.26 unit/mg, respectively. On the other hand, the Km and Vmax values against actinol as the substrate were 1.36 mM and 15.91 unit/mg, respectively.

The Km and Vmax values were calculated on the basis of the known Michaelis-Menten equation. Km is the concentration of the substrate that gives 50% of the Vmax of the enzyme reaction. The values provide a useful indication of the catalytic properties of the enzyme for the involved substrate.

11) Enzyme Purification Procedure

Purification of LR may, in principle, be effected by any combination of known purification methods, such as fractionation with precipitants, e.g. ammonium sulfate, polyethylene glycol, and the like, ion exchange chromatography, adsorption chromatography, gel-filtration chromatography, gel electrophoresis and salting out, and dialysis.

As set forth above, the LR provided by the present invention may be prepared by cultivating an appropriate microorganism in an aqueous nutrient medium under aerobic conditions, disrupting the cells of the microorganism, isolating, and purifying the LR from the cell-free-extract of the disrupted cells of the microorganism.

Microorganisms that may be used in the present invention include microorganisms belonging to the genus Corynebacterium which are capable of producing LR as defined hereinbefore. Functional equivalents, subcultures, mutants and variants of these microorganisms may also be used in the present invention.

In the present invention, a preferred strain of microorganism is *Corynebacterium aquaticum*, such as for example *Corynebacterium aquaticum* AKU611 (FERM BP-6448), a sample of which was deposited with the National Institute of Bioscience and Human-Technology, Agency of Industrial Science and Technology, Japan, on Aug. 4, 1998, under the terms of the Budapest Treaty. European Patent Application Nos. 98115564.1 and 99115723.1 also disclose certain characteristics of this strain.

The microorganism of the present invention may be cultured in a nutrient medium containing, for example, saccharides such as glucose and sucrose, alcohols such as ethanol and glycerol, fatty acids such as oleic acid and stearic acid, or esters thereof, or oils such as rapeseed oil and soybean oil as carbon sources; ammonium sulfate, sodium nitrate, peptone, amino acids, corn steep liquor, bran, yeast extract and the like as nitrogen sources; magnesium sulfate, sodium chloride, calcium carbonate, potassium monohydrogen phosphate, potassium dihydrogen phosphate and the like as inorganic salt sources; and malt extract, meat extract, and the like as other nutrient sources. The cultivation may be carried out aerobically, normally for a period of about 1 to about 7 days at a medium pH of about 3 to about 9 and a cultivation temperature of about 10° C. to about 40° C.

In the present invention, isolation and purification of the LR from the microorganism after cultivation may be effected by, for example, harvesting the cells from a liquid culture broth by centrifugation or filtration. The harvested cells are washed with water, physiological saline or a buffer solution having an appropriate pH. The washed cells are suspended in the buffer solution and disrupted, for example, by means of a homogenizer, sonicator, French press, or treatment with lysozyme to give a solution of disrupted cells. The LR is isolated and purified from the cell-free extract of disrupted cells.

As set forth above, the LR provided by the present invention is useful as a catalyst for the production of actinol from levodione. The reaction of the LR-catalyzed reduction of levodione to actinol is conveniently conducted at pH values of from about 6.0 to about 9.0 in the presence of NADH in a solvent. As a solvent, any buffer which maintains the pH in the range of about 6.0 to about 9.0, such as Tris-HCl buffer, phosphate buffer, bis-tris buffer, HEPES buffer and the like, is suitable.

A preferred temperature range for carrying out the reaction is from about 2° C. to about 30 ° C. The reaction usually gives the best results when the pH and the temperature are about 7.0 to about 8.0 and about 10° C. to about 25 ° C., respectively.

The concentration of levodione in the solvent depends on the other reaction conditions, but in general is from about 1 mM to about 2 M, preferably from about 10 mM to about 100 mM.

The amount of the LR and NADH present in the reaction mixture depends on the other reaction conditions, but in general is in each case independently about $10^{-4}$ to $10^{-6}$ of the amount of the substrate. When a regeneration system of NADH from NAD is coupled with the above reaction system, the reaction proceeds more efficiently.

In the reaction, the LR may also be used in an immobilized state with an appropriate carrier. Any means of immobilizing enzymes generally known in the art may be used to immobilize the LR to a carrier. For instance, the enzyme may be bound directly to a membrane, granules or the like of a resin having one or more functional groups, or it may be bound to the resin through bridging compounds having one or more functional groups, e.g. glutaraldehyde. Such enzyme immobilizing reactions are described, for example, on pages 369–394 of the $^2$nd Edition of Microbial Enzymes and Biotechnology (Elsevier Applied Science 1990; Ed. W. M. Fogarty and C. T. Kelly).

The following examples are provided to further illustrate methods of preparation of the enzyme of the present invention, as well as certain physical properties and uses thereof. These examples are illustrative only and are not intended to limit the scope of the invention in any way.

EXAMPLE 1

Preparation of LR

In the examples that follow, all the operations were performed at 4° C. The buffer was 10 mM potassium phosphate buffer (pH 7.0) containing 0.1 mM dithiothreitol unless otherwise stated.

(1) Cultivation of *Corynebacterium aquaticum* AKU 611 (FERM BP-6448)

One colony of *Corynebacterium aquaticum* AKU 611 (FERM BP-6448) on an agar plate was inoculated into 5 ml of a medium (pH 7.0) containing of D-glucose (1%), $KH_2PO_4$ (0.3%), $MgSO_4.7H_2O$ (0.02%), Peptone (1.5%), NaCl (0.2%) and yeast extract (0.1%) in a tube, and incubated for 20 hours at 30° C. This culture was inoculated into 500 ml of the same medium as above in a 2 l Sakaguchi flask, and incubated for 20 hours at 30° C. A 250 ml portion of the seed culture was inoculated into 20 l of the same medium in a jar fermenter MSJ-U3W (Marubishi Bioengineering, Tokyo, Japan). Cultivation was effected at 30° C. for 20 hours with aeration at the rate of 20 I/min. and agitation at 300 rpm. The culture thus obtained was centrifuged at 8,000 rpm for 20 minutes at 4° C. In total, 5 133.8 g of wet cells were obtained.

(2) Preparation of the Cell-free Extract

The wet cells (30 g) were suspended in 90 ml of the buffer, and sonicated for 1 hour at 190 W using a Kubota Insonator 201 sonicator (Kubota, Tokyo, Japan). After sonication, the sample was centrifuged at 16,000 rpm for 20 minutes. As a result, 80 ml of the cell-free extract containing 2,444 mg of protein were obtained.

(3) Ammonium Sulfate Precipitation

To the cell-free extract (80 ml) obtained in the previous step, ammonium sulfate was added until a 60% saturation concentration had been achieved. Then, the resulting precipitate was collected by centrifugation, solubilized in 15 ml of the buffer, and dialyzed four times against 5 l of the buffer. The total enzyme activity in this solution was 38.8 units.

(4) Diethylamninoethyl (Hereinafter Referred to as DEAE)-Sephacel Column Chromatography The dialyzed sample prepared as described above was applied to a DEAE-Sephacel column (2.8 cm in diameter and 18 cm in height; Amershamn Pharmnacia Biotech) which was equilibrated with the buffer. After washing the column with the same buffer, the enzyme was eluted with 600 ml of a linear gradient of NaCl (014 0.8 M). The active fractions were collected and concentrated by ultrafiltration (ultrafilter YM-10 with Amicon concentration apparatus (Amicon Inc., Beverly, Mass.) to 10 ml.

(5) Alkyl Superose Column Chromatography

To the sample from the previous step was added $(NH_4)_2SO_4$ to a final concentration of 2 M, and the mixture was filtered. An alkyl supersose IO/1OO column (I cm in diameter and 10 cm in height; Amersham Pharmacia Biotech) was equilibrated with the buffer containing 2 M $(NH_4)_2SO_4$, and applied by the above sample. The enzyme was eluted by a 150 ml of linear gradient of the buffer (2 to 0 M $(NH_4)_2SO_4$). The active fractions were collected, and dialyzed four times against 5 l of the buffer.

(6) MONO Q HR5/5 Column Chromatography

The dialyzed sample from the previous step was applied to a MONO Q 5/5 column (5 mm in diameter and 5 cm in height; Amersham Pharmacia Biotech) which was equilibrated by the buffer. The enzyme was eluted with 21 ml of a linear gradient of NaCl (0 to 0.8 M). The specific activity of the enzyme was not increased due to the de-activation of the enzyme during the dialyzation step before this chromatography. But the enzyme gave a homogenous band on SDS-PAGE analysis.

A summary of the enzyme purification steps is shown in Table 7.

TABLE 7

| Step | Total Activity (unit) | Total Protein (mg) | Specific Activity (unit/mg) | Yield (%) |
|---|---|---|---|---|
| Cell-free extract | — | 2444 | — | — |
| Precipitate by 60% $(NH_4)_2SO_4$ | 38.8 | 427 | 0.91 | 100 |
| DEAE Sephacel | 22 | 30 | 0.73 | 57 |
| Alkyl Superose | 15.2 | 0.92 | 16.5 | 39 |
| MONO Q 5/5 | 5.4 | 0.38 | 14.2 | 14 |

(7) Identification of the Reaction Product

The reaction mixture (3.33 ml) containing 50 mg of NADH, 833 µl of 1 M potassium phosphate buffer (pH 7.0), 2 ml of the enzyme sample from the purification step of DEAE Sephacel column chromatography, and 550 µl of distilled water was incubated at 30° C. To this reaction mixture, 10 Al of a 0.5 M levodione solution were added five times at 6 minute intervals. The reaction mixture was incubated for a further 5 minutes, and extracted with 1 ml of ethyl acetate. The extract was analyzed by gas chromatography (column: HR-20M (Shinwa, Kyoto, Japan) 0.25 mm Ø×30 m), column temperature: 160° C. (constant), injector temperature: 250° C., carrier gas: He (about 1 ml/min.). As a result, the product was identified as being actinol in comparison with a standard sample of actinol. When NADH was replaced with NADPH, only a trace amount of actinol was detected.

The invention being thus described, it will be obvious that the same may be varied in many ways. Such variations are not to be regarded as a departure from the spirit and scope of the invention and all such modifications are intended to be included within the scope of the following claims.

We claim:

1. An isolated and purified enzyme having levodione reductase activity wherein the enzyme comprises the following physico-chemical properties;
   (a) a molecular weight of about 142,000 to about 155,000±10,000 measured by gel filtration;

(b) a nicotinamide adenine dinucleotide (NAD/NADH) co-factor, (c) catalyzes the reduction of levodione to actinol;

(d) an optimum temperature of about 15° C. to about 20° C. at a pH of about 7.0;

(e) an optimum pH of about 7.5; and (f) wherein the enzyme is activated by a metal ion selected from the group consisting of $K^+$, $Cs^+$, $Rb^+$, $Na^+$ and $NH_4^+$.

2. The enzyme according to claim 1 consisting essentially of four homologous subunits each having a molecular weight of about 36,000±5,000 measured by SDS-polyacrylamide gel electrophoresis.

3. The enzyme according to claim 1 wherein the enzyme is obtained from Corynebacterium.

4. The enzyme according to claim 3 wherein the Corynebacterium is selected from the group consisting of *Corynebacterium aquaticum* AKU 611 (FERM BP-6448), and mutants thereof.

5. The enzyme according to claim 4 wherein the Corynebacterium is *Corynebacterium aquaticum* AKU 611 (FERM BP-6448).

6. An isolated and purified levodione reductase obtained from *Corynebacterium aquaticum* AKU 611 (FERM BP-6448) cells having the following properties:

(a) a molecular weight of about 142,000 to about 155,000±10,000 measured by gel filtration;

(b) a NAD/NADH cofactor;

(c) catalyzes the reduction of levodione to actinol;

(d) an optimum temperature of about 15° C. to about 20° C. at a pH of about 7.0;

(e) an optimum pH of about 7.5; and (f) the levodione reductase being activated by a metal ion selected from the group consisting of $K^+$, $Cs^+$, $Rb^+$, $Na^+$, and $NH_4^+$.

7. The levodione reductase according to claim 6 produced by the process comprising:

(a) culturing the *Corynebacterium aquaticum* AKU611 (FERM BP-6448) cells in a nutrient medium under aerobic conditions; and (b) preparing a cell free extract containing the levodione reductase by disrupting the cells.

8. The levodione reductase according to claim 7 wherein the levodione reductase is isolated from the cell free extract.

* * * * *

UNITED STATES PATENT AND TRADEMARK OFFICE
CERTIFICATE OF CORRECTION

PATENT NO. : 6,465,228 B1
DATED : October 15, 2002
INVENTOR(S) : Shigeru Nakamori et al.

It is certified that error appears in the above-identified patent and that said Letters Patent is hereby corrected as shown below:

<u>Title page,</u>
Item [75], Inventors, please change "Kyoto" to -- Kyoto-Fu --;
Item [56], References Cited, OTHER PUBLICATIONS, "Demain et al.," reference, please change "Manufal" to -- Manual --; "Demain et al.," reference, please change "Environment" to -- Environmental --;
Item [57], ABSTRACT,
Line 4, please change "(AND/" to -- (NAD/ --;
Lines 13 and 18, please italicize "Corynebacterium";

<u>Column 11,</u>
Line 2, please change the comma to a semicolon;
Line 15, please italicize "Corynebacterium";
Lines 16-17, please italicize "Corynebacterium";
Lines 20-21, please italicize "Corynebacterium".

Signed and Sealed this

Thirtieth Day of December, 2003

JAMES E. ROGAN
*Director of the United States Patent and Trademark Office*